(12) United States Patent
Freyne et al.

(10) Patent No.: US 8,476,289 B2
(45) Date of Patent: Jul. 2, 2013

(54) AZA-BICYCLOHEXYL SUBSTITUTED INDOLYL ALKYL AMINO DERIVATIVES AS NOVEL INHIBITORS OF HISTONE DEACETYLACE

(75) Inventors: Eddy Jean Edgard Freyne, Rumst (BE); Isabelle Noëlle Constance Pilatte, Louviers (FR); Patrick René Angibaud, Fontaine-Bellenger (FR)

(73) Assignee: Janssen Pharmaceutica NV, Beerse (BE)

( * ) Notice: Subject to any disclaimer, the term of this patent is extended or adjusted under 35 U.S.C. 154(b) by 223 days.

(21) Appl. No.: 12/934,894

(22) PCT Filed: Mar. 26, 2009

(86) PCT No.: PCT/EP2009/053566
§ 371 (c)(1),
(2), (4) Date: Sep. 27, 2010

(87) PCT Pub. No.: WO2009/118370
PCT Pub. Date: Oct. 1, 2009

(65) Prior Publication Data
US 2011/0015218 A1    Jan. 20, 2011

(30) Foreign Application Priority Data
Mar. 27, 2008   (EP) .................................... 08153370

(51) Int. Cl.
*C07D 401/14* (2006.01)
*A61K 31/506* (2006.01)

(52) U.S. Cl.
USPC ......... 514/275; 514/339; 544/331; 546/277.4

(58) Field of Classification Search
USPC ................. 544/331; 546/277.4; 514/275, 339
See application file for complete search history.

(56) References Cited

U.S. PATENT DOCUMENTS

| | | | |
|---|---|---|---|
| 2005/0234033 A1 | 10/2005 | Anandan et al. | |
| 2008/0132459 A1 | 6/2008 | Moradei et al. | |

FOREIGN PATENT DOCUMENTS

| | | |
|---|---|---|
| EP | 1485378 B1 | 7/1985 |
| EP | 0827742 A1 | 3/1998 |
| EP | 1485099 B1 | 12/2004 |
| EP | 1485348 B1 | 12/2004 |
| EP | 1485354 B1 | 12/2004 |
| EP | 1485364 B1 | 12/2004 |
| EP | 1485365 B1 | 12/2004 |
| EP | 1485370 B1 | 12/2004 |
| EP | 1492534 B1 | 1/2005 |
| EP | 1611088 B1 | 1/2006 |
| WO | WO 03/066579 A2 | 8/2003 |
| WO | WO 03/076400 A1 | 9/2003 |
| WO | WO 03/076438 A1 | 9/2003 |
| WO | WO 03/087057 A1 | 10/2003 |
| WO | WO 2004/009536 A1 | 1/2004 |
| WO | WO 2004/013130 A1 | 2/2004 |
| WO | WO 2004/028447 A2 | 4/2004 |
| WO | WO 2004/063146 A1 | 7/2004 |
| WO | WO 2004/063169 A1 | 7/2004 |
| WO | WO 2004/072047 A1 | 8/2004 |
| WO | WO 2004/082638 A2 | 9/2004 |
| WO | WO 2004/092115 A2 | 10/2004 |
| WO | WO 2005/030704 A1 | 4/2005 |
| WO | WO 2005/040101 A1 | 5/2005 |
| WO | WO 2005/040161 A1 | 5/2005 |
| WO | WO 2005/092899 A1 | 10/2005 |
| WO | WO 2006/010750 A1 | 2/2006 |
| WO | WO 2006/123121 A1 | 11/2006 |
| WO | WO 2007/045844 A1 | 4/2007 |
| WO | WO 2007/055942 A2 | 5/2007 |
| WO | WO 2007/082878 A1 | 7/2007 |
| WO | WO 2007/082880 A1 | 7/2007 |
| WO | WO 2007/082882 A1 | 7/2007 |
| WO | WO 2007/091703 A1 | 8/2007 |
| WO | WO 2007/100657 A2 | 9/2007 |
| WO | WO 2009/058298 * | 5/2009 |

OTHER PUBLICATIONS

Takai et al., PubMed Abstract (Cancer 101(12):2760-70), Dec. 2004.*
Simone, Oncology: Introduction, Cecil Textbook of Medicine, 20th Edition, vol. 1, pp. 1004-101 O, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Glaser, HDAC inhibitors: Clinical update and mechanism-based potential, Biochemical Pharmacology, 74, pp. 659-671, 2007.*
Abmyr, S., M., et al. "The Pseudorabies Immediate Early Protein Stimulates in Vitro Transcription by Facilitating TFIID: Promoter Interactions", Genes & Development, vol. 2 (1988) pp. 542-533.
Dignam, J. D., et al., "Accurate Transcription Initiation by RNA Polymerase II in a Soluble Extract from Isolated Mammalian Nuclei", Nucleic Acids Research, vol. 11, No. 5 (1983) pp. 1475-1489.

(Continued)

Primary Examiner — Deepak Rao

(57) ABSTRACT

This invention comprises the novel compounds of formula (I)

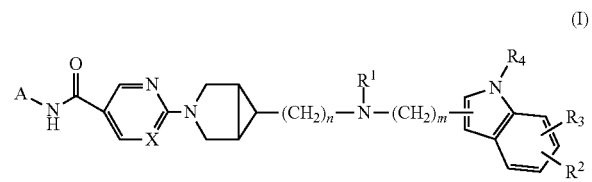

wherein $R^1$, $R^2$, $R^3$, $R^4$, A and X have defined meanings, having histone deacetylase inhibiting enzymatic activity; their preparation, compositions containing them and their use as a medicine.

9 Claims, No Drawings

OTHER PUBLICATIONS

Finney, D. J., "Graded Response: The Linear Dosage-Response Curve", Probit Analysis, 2nd Edition, Chapter 10 (1962), Cambridge Publishing Press, 16 page article.

Finnin, M. S., et al. "Structures of a Histone Deacetylase Homologue Bound to the TSA and SAHA Inhibitors", Nature, vol. 401, (1999) pp. 188-193.

Mai, A., et al. "Histone Deacetylation in Epigenetics: An Attractive Target for Anticancer Therapy", Medicinal Research Reviews, vol. 25, No. 3 (2005) pp. 261-309.

Mosmann, T., "Rapid Colorimetric Assay for Cellular Growth and Survival: Application to Proliferation and Cytotoxicity Assays", Journal of Immunological Methods, vol. 65 (1983) pp. 55-63.

International Search Report mailed Jun. 3, 2009 for corresponding International Application No. PCT/EP2009/053566.

* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MOD_RES
<222> LOCATION: (9)..(9)
```

```
<223> OTHER INFORMATION: AMIDATION

<400> SEQUENCE: 1

Lys Gly Ala Lys Arg His Arg Lys Val
1               5
```

US 8,476,289 B2

AZA-BICYCLOHEXYL SUBSTITUTED INDOLYL ALKYL AMINO DERIVATIVES AS NOVEL INHIBITORS OF HISTONE DEACETYLACE

CROSS REFERENCE TO RELATED APPLICATIONS

This application is a national stage of PCT Application No. PCT/EP2009/053566, filed Mar. 26, 2009, which claims priority for EPO Patent Application No. 08153370.5, filed Mar. 27, 2008, all of which are hereby incorporated by reference in their entirety.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

Nuclear histones are known as integral and dynamic components of the machinery responsible for regulating gene transcription and other DNA-templated processes such as replication, repair, recombination, and chromosome segregation. They are the subject of post-translational modifications including acetylation, phosphorylation, methylation, ubiquitination, and ADP-ribosylation.

Histone deacetylase(s), herein referred to as "HDACs", are enzymes that catalyze the removal of the acetyl modification on lysine residues of proteins, including the core nucleosomal histones H2A, H2B, H3 and H4. Together with histone acetyltransferase(s), herein referred to as "HATs", HDACs regulate the level of acetylation of the histones. The balance of acetylation of nucleosomal histones plays an important role in transcription of many genes. Hypoacetylation of histones is associated with condensed chromatin structure resulting in the repression of gene transcription, whereas acetylated histones are associated with a more open chromatin structure and activation of transcription.

Eleven structurally related HDACs have been described and fall into three classes. Class I HDACs consist of HDAC 1, 2, 3, 8, class II HDACs consist of HDAC 4, 5, 6, 7, 9 and 10 whereas HDAC 11 represents class IV. Members of the third class of HDACs are structurally unrelated to the class I, II and class IV HDACs. Class I/II/IV HDACs operate by zinc-dependent mechanisms, whereas class III HDACs are NAD-dependent.

In addition to histones, other proteins have also been the substrate for acetylation, in particular transcription factors such as p53, GATA-1 and E2F; nuclear receptors such as the glucocorticoid receptor, the thyroid receptors, the estrogen receptors; and cell-cycle regulating proteins such as pRb. Acetylation of proteins has been linked with protein stabilization, such as p53 stabilization, recruitment of cofactors and increased DNA binding. p53 is a tumour suppressor that can induce cell cycle arrest or apoptosis in response to a variety of stress signals, such as DNA damage. The main target for p53-induced cell cycle arrest seems to be the p21 gene. Next to its activation by p53, p21 has been identified by virtue of its association with cyclin/cyclin-dependent kinase complexes resulting in cell cycle arrest at both G1 and G2 phases, its up-regulation during senescence, and its interaction with the proliferating cell nuclear antigen.

The study of inhibitors of HDACs indicates that they play an important role in cell cycle arrest, cellular differentiation, apoptosis and reversal of transformed phenotypes.

The inhibitor Trichostatin A (TSA), for example, causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 Mar., 1998).

The pharmacophore for HDAC inhibitors consists of a metal-binding domain, which interacts with the zinc-containing active site of HDACs, a linker domain, and a surface recognition domain or capping region, which interacts with residues on the rim of the active site.

Inhibitors of HDACs have also been reported to induce p21 gene expression. The transcriptional activation of the p21 gene by these inhibitors is promoted by chromatin remodelling, following acetylation of histones H3 and H4 in the p21 promotor region. This activation of p21 occurs in a p53-independent fashion and thus HDAC inhibitors are operative in cells with mutated p53 genes, a hallmark of numerous tumours.

In addition HDAC inhibitors can have indirect activities such as augmentation of the host immune response and inhibition of tumor angiogenesis and thus can suppress the growth of primary tumors and impede metastasis (Mai et al., Medicinal Research Reviews, 25: 261-309, 2005).

In view of the above, HDAC inhibitors can have great potential in the treatment of cell proliferative diseases or conditions, including tumours with mutated p53 genes.

Patent application EP1472216 published on Aug. 14, 2003 discloses bicyclic hydroxamates as inhibitors of histone deacetylase.

Patent applications EP1485099, EP1485348, EP1485353, EP1485354, EP1485364, EP1485365, EP1485370, EP1485378 published on 18 Sep., 2003, amongst others, disclose substituted piperazinylpyrimidinylhydroxamic acids as inhibitors of histone deacetylase furthermore EP1485365 discloses R306465.

Patent application EP1492534 published on 9 Oct., 2003, discloses carbamic acid compounds comprising a piperazine linkage, as HDAC inhibitors.

Patent application EP1495002 published on 23 Oct., 2003, disclose substituted piperazinyl phenyl benzamide compounds, as histone deacetylase inhibitors.

Patent application WO04/009536 published on 29 Jan., 2004, discloses derivatives containing an alkyl linker between the aryl group and the hydroxamate, as histone deacetylase inhibitors.

Patent application EP1525199 published on 12 Feb., 2004, discloses (hetero)arylalkenyl substituted bicyclic hydroxamates, as histone deacetylase inhibitors.

Patent application EP1581484 published on 29 Jul. 2004, discloses derivatives of N-hydroxy-benzamide derivatives with anti-inflammatory and antitumour activity.

Patent application EP1585735 published on 29 Jul. 2004, discloses substituted aryl hydroxamate derivatives as histone deacetylase inhibitors.

Patent application WO04/072047 published on 26 Aug. 2004, discloses indoles, benzimidazoles and naphimidazoles as histone deacetylase inhibitors.

Patent application EP1608628 published on 30 Sep. 2004, discloses hydroxamates linked to non-aromatic heterocyclic ring systems as histone deacetylase inhibitors.

Patent application EP1611088 published on 28 Oct. 2004, discloses hydroxamate derivatives as histone deacetylase inhibitors.

Patent application EP1546326 published on 31 Mar. 2005, discloses benzimidazoles as histone deacetylase inhibitors.

Patent applications WO05/030704 and EP1663953 published on 7 Apr. 2005, discloses benzamides as histone deacetylase inhibitors.

Patent application EP1685094 published on 6 May 2005, discloses acylurea connected and sulfonylurea connected hydroxamates as histone deacetylase inhibitors.

Patent application EP1682538 also published on 6 May 2005, discloses biaryl linked hydroxamates as histone deacetylase inhibitors.

Patent application EP1735319 published on 6 Oct., 2005 describes novel inhibitors of histone deacetylases.

Patent application EP1781639 published on 2 Feb. 2006 discloses substituted indolyl alkyl amino derivatives as histone deacetylase inhibitors.

Patent application US05/0234033 A1 published on 20 Oct., 2007 discloses, among others, azabicyclohexyl derivatives as histone deacetylase inhibitors Patent application EP1881977 published on 23 Nov., 2006 discloses, among others, azabicyclohexyl derivatives as histone deacetylase inhibitors.

Patent application WO07/045,844 published on 26 Apr., 2007 discloses benzamide compounds useful as histone deacetylase inhibitors.

Patent application WO07/055,942 published on 18 May, 2007 relates to a novel class of nicotinamides that can inhibit histone deacetylase.

Patent applications WO07/082,878, WO07/082,880 and WO07/082,882 published on 26 Jul., 2007 discloses pyrimidines derivatives as inhibitors of histone deacetylase.

Patent application WO07/091,703 published on 16 Aug., 2007 discloses pyrazinylhydroxyacrylamides as histone deacetylase inhibitors.

Patent application WO07/100,657 published on 7 Sep., 2007 discloses (hetero)arylcarboxamides as inhibitors of histone deacetylase.

The compounds of the present invention differ from the prior art in structure, in their pharmacological activity and/or pharmacological potency.

This invention concerns compounds of formula (I)

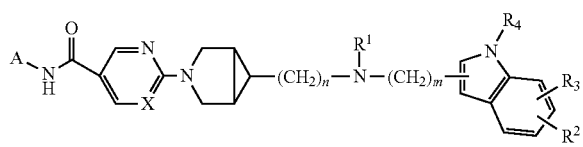

the N-oxide forms, the pharmaceutically acceptable addition salts and the stereo-chemically isomeric forms thereof, wherein each n is an integer with value 0, 1 or 2 and when n is 0 then a direct bond is intended;
each m is an integer with value 1 or 2;
X is independently N or CH;
A is hydroxy or a radical of formula:

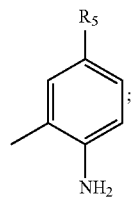

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;

$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;

$R^3$ is hydrogen, halo, $C_{1-6}$alkyl, or $C_{1-6}$alkyloxy; or
when $R^2$ and $R^3$ are on adjacent carbon atoms, they can form the bivalent radical:

$$—O—CH_2—O— \quad (a\text{-}2);$$

$R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl; or
when $R^2$ is on the 7-position of the indolyl then $R^2$ and $R^4$ together can form the bivalent radical;

$$—(CH_2)_2— \quad (a\text{-}3), or$$

$$—(CH_2)_3— \quad (a\text{-}4);$$

$R^5$ is hydrogen or thiophenyl.

Lines drawn into the bicyclic ring systems from substituents indicate that the bonds may be attached to any of the suitable ring atoms of the bicyclic ring system.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; $C_{1-2}$alkyl straight chain saturated hydrocarbon radicals having 1 or 2 carbon atoms such as, e.g. methyl or ethyl; $C_{1-6}$alkyl defines $C_{1-2}$alkyl and straight and branched chain saturated hydrocarbon radicals having from 3 to 6 carbon atoms such as, e.g. propyl, butyl, 1-methylethyl, 2-methylpropyl, pentyl, 2-methyl-butyl, hexyl, 2-methylpentyl and the like; and polyhalo$C_{1-6}$alkyl defines $C_{1-6}$alkyl containing three identical or different halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{3-6}$cycloalkyl includes cyclic hydrocarbon groups having from 3 to 6 carbons, such as cyclopropyl, cyclobutyl, cyclopentyl, cyclopentenyl, cyclohexyl, cyclohexenyl, and the like.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures, which are not interchangeable, which the compounds of formula (I) may possess. Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 HDAC-10 and HDAC-11. The histone deacetylase can also be derived from a protozoal or fungal source.

A first group of interesting compounds consists of those compounds of formula (I) wherein one or more of the following restrictions apply:
a) A is hydroxy;
b) $R^1$ is hydrogen, $C_{1-6}$alkyl, hydroxy$C_{1-6}$alkyl, $C_{1-6}$alkylsulfonyl, or mono- or di($C_{1-6}$alkyl)aminosulfonyl;
c) $R^3$ is hydrogen; or
d) $R^4$ is hydrogen, $C_{1-6}$alkyl, $C_{3-6}$cycloalkyl or $C_{3-6}$cycloalkylmethyl.

A second group of interesting compounds consists of those compounds of formula (I) or the compounds of the first group of interesting compounds wherein one or more of the following restrictions apply:
a) each n is an integer with value 0 or 1;
b) each m is an integer with value 1;
c) X is independently N;
d) A is hydroxy;
e) $R^1$ is hydrogen;
f) $R^2$ is hydrogen, halo or cyano;
g) $R^3$ is hydrogen; or
g) $R^4$ is $C_{1-6}$alkyl.

A third group of interesting compounds consists of those compounds of formula (I), the compounds of the first group of interesting compounds or the compounds of the second group of interesting compounds wherein one or more of the following restrictions apply:
a) each n is an integer with value 1;
b) each m is an integer with value 1;
c) X is independently N;
d) A is hydroxy;
e) $R^1$ is hydrogen;
f) $R^2$ is hydrogen;
g) $R^3$ is hydrogen; or
g) $R^4$ is $C_{1-6}$alkyl.

A group of preferred compounds consists of those compounds of formula (I) wherein each n is an integer with value 0 or 1; each m is an integer with value 1; X is independently N; A is hydroxy; $R^1$ is hydrogen; $R^2$ is hydrogen, halo or cyano; $R^3$ is hydrogen; and $R^4$ is $C_{1-6}$alkyl.

A group of more preferred compounds consists of those compounds of formula (I) wherein each n is an integer with value 1; each m is an integer with value 1; X is independently N; A is hydroxy; $R^1$ is hydrogen; $R^2$ is hydrogen; $R^3$ is hydrogen; and $R^4$ is $C_{1-6}$alkyl.

The most preferred compound is compound No 1.

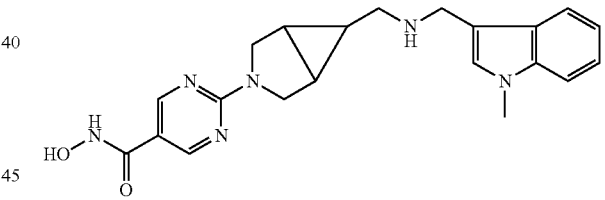

The compounds of formula (I) and (II), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art or as described in patent applications EP1485099, EP1485348, EP1485353, EP1485354, EP1485364, EP1485365, EP1485370, and EP1485378. Some preparation methods will be described hereinafter in more detail. Other methods for obtaining final compounds of formula (I) are described in the examples.

a) Hydroxamic acids of formula (I), herein referred to as compounds of formula (I-a) may be prepared by reacting an intermediate of formula (II), wherein Q is tetrahydropyranyloxyaminocarbonyl, herein referred to as intermediates of formula (II-a), with an appropriate acid, such as, for example, trifluoro acetic acid. Said reaction is performed in an appropriate solvent, such as, for example, methanol or dichloromethane.

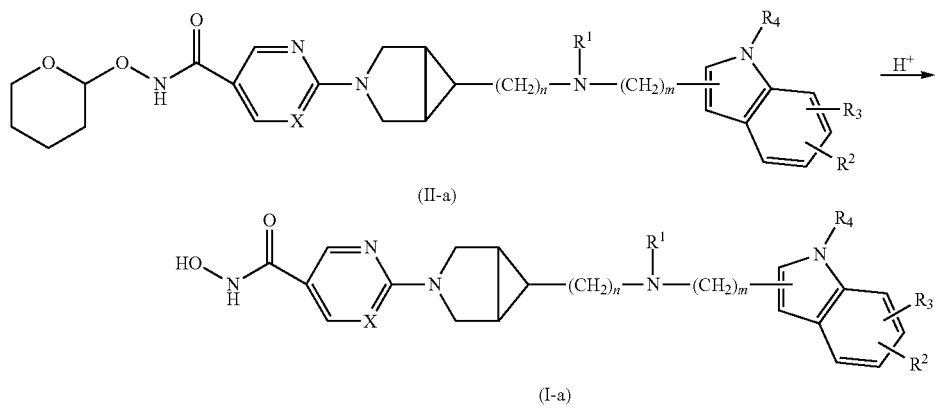

(II-a)

(I-a)

b) Compounds of formula (I) wherein A is a radical of formula (a-1), herein referred to as compounds of formula (I-b), may be prepared by reacting an intermediate of formula (IV) wherein M represents hydrogen or an alkali metal for example sodium or lithium, with an aniline of formula (III), in the presence of a base such as for example triethylamine, and benzotriazol-1-yloxy-tripyrrolidino-phosphonium hexafluorophosphate (PyBOP). Said reaction is performed in an appropriate solvent, such as, for example, tetrahydrofuran or dichloromethane or a mixture thereof The present invention also concerns intermediates of formula (II)

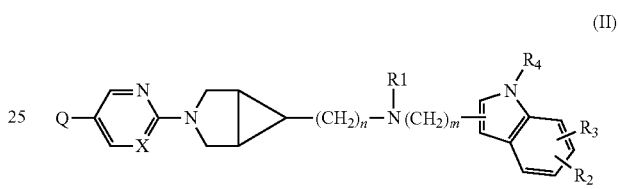

(II)

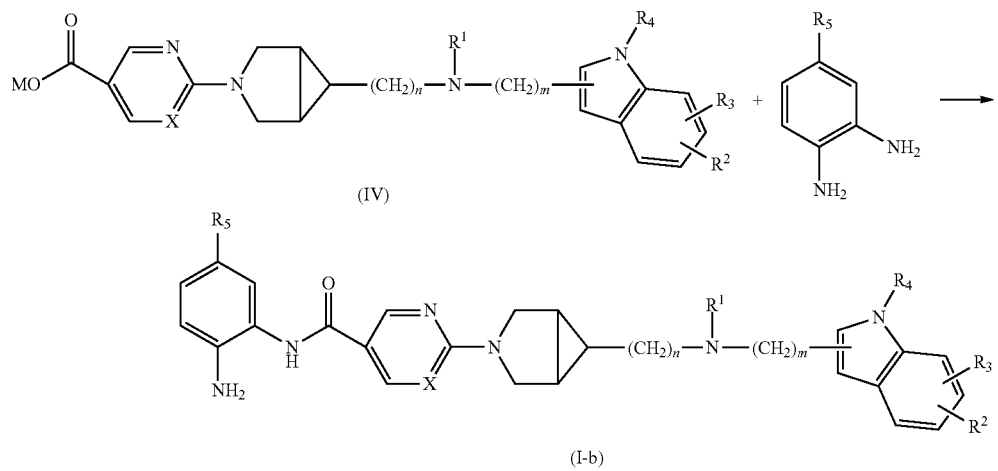

(IV)

(I-b)

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

the N-oxide forms, the pharmaceutically acceptable addition salts and the stereo-chemically isomeric forms thereof, wherein each n is an integer with value 0, 1 or 2 and when n is 0 then a direct bond is intended;

each m is an integer with value 1 or 2;

each X is independently N or CH;

Q is $C_{1-2}$alkyloxycarbonyl, hydroxycarbonyl or tetrahydropyranyloxyaminocarbonyl.

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;

$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;

$R^3$ is hydrogen, halo, $C_{1-6}$alkyl, or $C_{1-6}$alkyloxy; and when $R^2$ and $R^3$ are on adjacent carbon atoms, they can form the bivalent radical:

—O—CH$_2$—O—                           (a-2);

$R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl; or when $R^2$ is on the 7-position of the indolyl then $R^2$ and $R^4$ together can form the bivalent radical;

—(CH$_2$)$_2$—                                  (a-3), or

—(CH$_2$)$_3$—                                    (a-4);

$R^5$ is hydrogen or thiophenyl.

Groups of interesting, preferred, more preferred and most preferred compounds can be defined for the compounds of formula (II), in accordance with the groups defined for the compounds of formula (I).

a) Intermediates of formula (II-a) may be prepared by reacting an intermediate of formula (IV) in which M represents an alkali metal cation such as sodium with an intermediate of formula (V) in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

reospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including

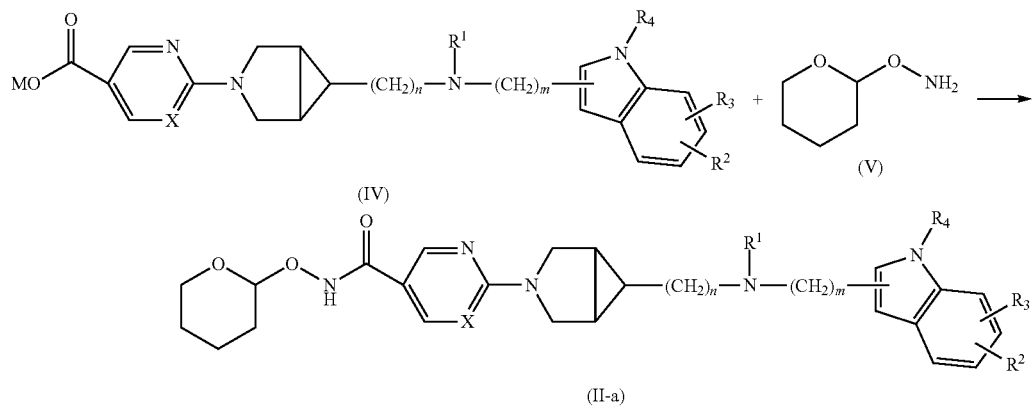

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stenon-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:

a) the sensitisation of tumours to radiotherapy by administering the compound according to the invention before, during or after irradiation of the tumour for treating cancer;

b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;
c) inhibiting smooth muscle cell proliferation including vascular proliferative disorders, atherosclerosis and restenosis;
d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia areata, scleroderma, exanthema, eczema, dermatomyositis, acne, diabetes, systemic lupus erythematosis, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating a cardiac dysfunction;
h) inhibiting immunosuppressive conditions such as the treatment of HIV infections;
i) treating renal dysfunction;
j) suppressing endocrine disorders;
k) inhibiting dysfunction of gluconeogenesis;
l) treating a neuropathology for example Parkinson's disease or a neuropathology that results in a cognitive disorder, for example, Alzheimer's disease or polyglutamine related neuronal diseases;
m) treating psychiatric disorders for example schizophrenia, bipolar disorder, depression, anxiety and psychosis;
n) inhibiting a neuromuscular pathology, for example, amylotrophic lateral sclerosis;
o) treating spinal muscular atrophy;
p) treating other pathologic conditions amenable to treatment by potentiating expression of a gene;
q) enhancing gene therapy;
r) inhibiting adipogenesis;
s) treating parasitosis such as malaria.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;

taxane compounds for example paclitaxel or docetaxel;
topoisomerase I inhibitors such as camptothecin compounds for example irinotecan or topotecan;
topoisomerase II inhibitors such as anti-tumour podophyllotoxin derivatives for example etoposide or teniposide;
anti-tumour vinca alkaloids for example vinblastine, vincristine or vinorelbine;
anti-tumour nucleoside derivatives for example 5-fluorouracil, gemcitabine or capecitabine;
alkylating agents such as nitrogen mustard or nitrosourea for example cyclophosphamide, chlorambucil, carmustine or lomustine;
anti-tumour anthracycline derivatives for example daunorubicin, doxorubicin, idarubicin or mitoxantrone;
HER2 antibodies for example trastuzumab;
estrogen receptor antagonists or selective estrogen receptor modulators for example tamoxifen, toremifene, droloxifene, faslodex or raloxifene;
aromatase inhibitors such as exemestane, anastrozole, letrazole and vorozole;
differentiating agents such as retinoids, vitamin D and retinoic acid metabolism blocking agents (RAMBA) for example accutane;
DNA methyl transferase inhibitors for example azacytidine;
kinase inhibitors for example flavoperidol, imatinib mesylate or gefitinib;
farnesyltransferase inhibitors;
other HDAC inhibitors;
inhibitors of the ubiquitin-proteasome pathway for example Velcade; or
Yondelis.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topoisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topoisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus Strep. peuticus var. caesius and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:

- carboxylates for example butyrate, cinnamic acid, 4-phenylbutyrate or valproic acid;
- hydroxamic acids for example suberoylanilide hydroxamic acid (SAHA), piperazine containing SAHA analogues, biaryl hydroxamate A-161906 and its carbozolylether-, tetrahydropyridine- and tetralone-analogues, bicyclic aryl-N-hydroxycarboxamides, pyroxamide, CG-1521, PXD-101, sulfonamide hydroxamic acid, LAQ-824, LBH-589, trichostatin A (TSA), oxamflatin, scriptaid, scriptaid related tricyclic molecules, m-carboxy cinnamic acid bishydroxamic acid (CBHA), CBHA-like hydroxamic acids, trapoxin-hydroxamic acid analogue, R306465 and related benzoyl- and heteroaryl-hydroxamic acids, aminosuberates and malonyldiamides;
- cyclic tetrapeptides for example trapoxin, apidicin, depsipeptide, spiruchostatin-related compounds, RedFK-228, sulfhydryl-containing cyclic tetrapeptides (SCOPs), hydroxamic acid containing cyclic tetrapeptides (CHAPs), TAN-174s and azumamides;
- benzamides for example MS-275 or CI-994, or depudecin.

The term "inhibitors of the ubiquitin-proteasome pathway" is used to identify compounds that inhibit the targeted destruction of cellular proteins in the proteasome, including cell cycle regulatory proteins.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination according to the invention of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

Trastuzumab is advantageously administered in a dosage of 1 to 5 mg per square meter (mg/m$^2$) of body surface area, particularly 2 to 4 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day.

Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

EXPERIMENTAL PART

The following examples are provided for purposes of illustration. Hereinafter, "DCM" is defined as dichloromethane, "DMSO" is defined as dimethylsulfoxide, "EDC" is defined as N-(ethylcarbonimidoyl)-N,N-dimethyl-1,3-propanediamine, monohydrochloride, "HOBt" is defined as 1-hydroxy-1H-benzotriazole, "MeOH" is defined as methanol, "TFA" is defined as trifluoroacetic acid and "THF" is defined as tetrahydrofuran.

A. Preparation of the Intermediate Compounds

Example A1 a) Preparation of Intermediate 1

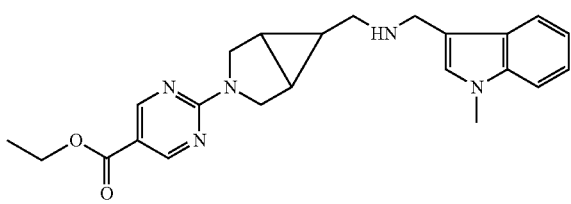 [SMILES: CCOC(=O)c1cnc(N2CC3C(CNCc4cn(C)c5ccccc45)C3C2)nc1]

A mixture of 2-(6-Aminomethyl-3-aza-bicyclo[3.1.0]hex-3-yl)-pyrimidine-5-carboxylic acid ethyl ester (0.11 g, 0.00042 mol) and 1-methyl-1H-indole-3-carboxaldehyde (0.1 g, 0.0 0063 mol) in MeOH (5 mL) was stirred and refluxed for 48 hours, then cooled to 10° C. DCM (5 mL) was added and sodium tetrahydroborate (0.025 g, 0.00067 mol) was added portionwise. The mixture was stirred at room temperature for 4 hours poured out into water and extracted with DCM. The organic layer was separated, dried (MgSO$_4$), filtered, and the solvent was evaporated. The residue (0.17 g) was purified by column chromatography over silica gel (15-40 μm) (eluent: DCM/MeOH/NH$_4$OH 95/5/0.5). The pure fractions were collected and the solvent was evaporated, yielding 0.03 g (18%) of intermediate 1.

$^1$H NMR (300 MHz, CDCl$_3$): 0.75-0.9 (m, 1H); 1.3 (t, J=7.2 Hz, 3H); 1.5 (s, 2H); 2.6 (d, J=7.2 Hz, 2H); 3.45-3.6 (m, 2H); 3.7 (s, 3H); 3.8-4.0 (m, 4H); 4.3 (q, J=7.2 Hz, 2H); 6.95 (s, 1H); 7.1 (t, J=7.5 Hz, 1H); 7.15-7.3 (m, 3H); 7.5 (d, J=7.5 Hz, 1H); 8.7 (s, 2H).

b) Preparation of Intermediate 2

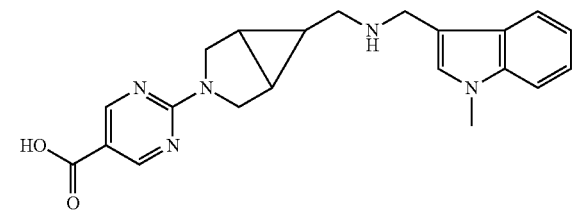 [SMILES: Cn1cc(CNCC2C3CN(c4ncc(C(=O)O)cn4)CC23)c2ccccc21]

A mixture of intermediate 1 (0.03 g, 0.00074 mol) and sodium hydroxide 1M (0.59 mL, 0.0006 mol) in THF (1 mL) and MeOH (175 μL) was stirred at room temperature for 24 hours. The solvents were evaporated and the resultant aqueous solution was acidified to pH: 3-4 with HCl 1N, the residue was evaporated till dryness, yielding 0.028 g of intermediate 2.

$^1$H NMR (400 MHz, d$_6$-DMSO): 0.9 (m, 1H); 1.8 (s, 2H); 2.9 (d, J=7.6 Hz, 2H); 3.55 (d, J=11.6 Hz, 2H); 3.8 (s, 3H); 3.85 (d, J=11.6 Hz, 2H); 4.25 (s, 2H); 7.1 (t, J=7.6 Hz, 1H); 7.2 (t, J=7.6 Hz, 1H); 7.45 (d, J=7.6 Hz, 1H); 7.5 (s, 1H); 7.75 (d, J=7.6 Hz, 1H); 8.7 (s, 2H).

c) Preparation of Intermediate 3

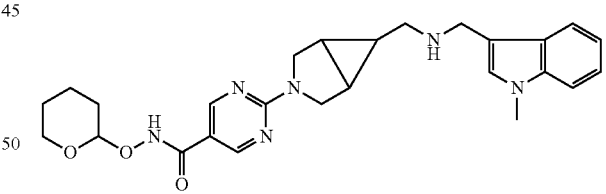

EDC (0.0551 g, 0.000355 mol), HOBt (0.0479 g, 0.000355 mol) then triethylamine 0.063 mL, 0.00044 mol) and O-(tetrahydro-2H-pyran-2-yl)-hydroxylamine (0.0416 g, 0.000355 mol) were added at room temperature to a mixture of intermediate 2 (0.028 g, 0.000074 mol) in DCM (0.8 mL) and THF (4 mL) under N$_2$ flow. After stirring at room temperature for 7 days. The same quantities of EDC, HOBT, triethylamine and O-(tetrahydro-2H-pyran-2-yl)-hydroxylamine were again added, the mixture was stirred at room temperature for another 7 days. The solution was poured out into ice water and extracted with DCM. The organic layer was separated, dried (MgSO$_4$), filtered, and the solvent was evaporated. The residue (0.155 g) was purified by column chromatography over silica gel (3.5 μm) (eluent: DCM/MeOH/NH$_4$OH 98/2/0.2).

The pure fractions were collected and the solvent was evaporated. till dryness yielding 0.016 g (46%) of intermediate 3.

¹H NMR (400 MHz, d₆-DMSO): 0.7-0.85 (m, 1H); 1.5-1.75 (m, 8H); 3.35 (s, 2H); 3.5-3.55 (m, 3H); 3.75 (s, 3H); 3.8 (d, J=11.6 Hz, 2H); 3.85 (s, 2H); 3.95-4.05 (m, 1H); 4.9-4.95 (m, 1H); 7 (t, J=7.6 Hz, 1H); 7.1 (t, J=7.6 Hz, 1H); 7.2 (s, 1H); 7.35 (d, J=7.6 Hz, 1H); 7.6 (d, J=7.6 Hz, 1H); 8.65 (s, 2H); 11.3 (br s, 1H).

Example A2 a) Preparation of Intermediate 4

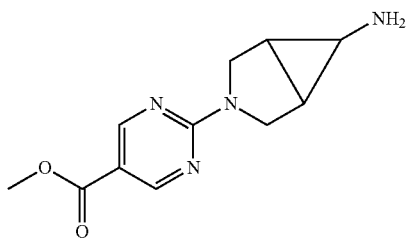 [SMILES: COC(=O)c1cnc(N2CC3C(N)C3C2)nc1]

Under N₂ at room temperature, 2-chloro-pyrimidine-5-carboxylic acid methyl ester (4.75 g, 0.028 mol) was added portionwise to a solution of 3-aza-bicyclo[3.1.0]hex-6-ylamine (3 g, 0.0306 mol) and potassium carbonate (6.327 g, 0.046 mol) in acetonitrile (80 mL). The solution was stirred at room temperature for 3 hours. The solution was poured out into cooled water, the product was extracted with DCM, the organic layer was dried over MgSO4, filtered and evaporated to dryness. The residue (3 g) was purified by column chromatography over silica gel (15-40 μm) (eluent: DCM/MeOH/NH₄OH 97/3/0.5). The pure fractions were collected and the solvent was evaporated till dryness. The residue (1.60 g) was taken up with diethyl ether. The precipitate was filtered and dried, yielding 1.55 g (22%) of intermediate 4, melting point: 149° C.

¹H NMR (400 MHz, d₆-DMSO) 1.55 (s, 2H); 1.9 (br s, 2H); 1.95 (s, 1H); 3.5-3.6 (m, 2H); 3.7 (d, J=11.6 Hz, 2H); 3.8 (s, 3H); 8.75 (s, 2H).

b) Preparation of Intermediate 5

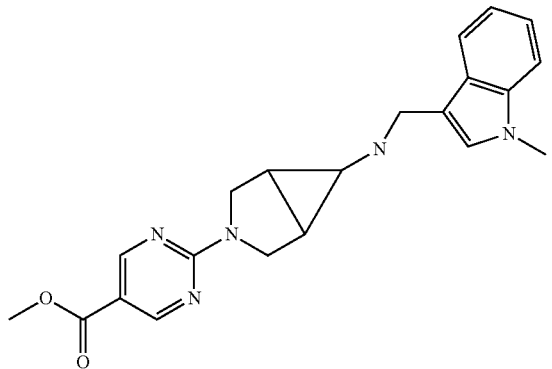

A solution of intermediate 4 (1.5 g, 0.0064 mol) and 1-methylindole-3-carboxaldehyde (1.53 g, 0.0096 mol) in D (50 mL) was heated for 24 hours. The solution was cooled at 5° C., DCM (50 mL) and sodium tetrahydroborate (0.39 g, 0.01025 mol) were added. The solution was stirred at room temperature for 4 hours. The solution was poured out into cooled water and extracted with DCM. The organic layer was dried over MgSO₄, filtered and evaporated to dryness. The residue (5.2 g) was purified by column chromatography over silica gel (15-40 μm) (eluent: DCM/MeOH/NH₄OH 97/3/0.1). The pure fractions were collected and the solvent was evaporated till dryness. The residue (1.73 g, 72%) was taken up with diethyl ether. The precipitate was filtered and dried, yielding 1.6 g (66%) of intermediate 5, melting point: 179° C.

¹H NMR (400 MHz, d₆-DMSO) 1.7 (s, 2H); 1.8 (s, 1H); 3.5-3.6 (m, 2H); 3.7-3.75 (m, 5H); 3.8 (s, 3H); 3.85 (s, 2H); 7.0 (t, J=7.6 Hz, 1H); 7.1 (t, J=7.6 Hz, 1H); 7.2 (s, 1H); 7.35 (d, J=7.6 Hz, 1H); 7.6 (d, J=7.6 Hz, 1H); 8.75 (s, 2H).

c) Preparation of Intermediate 6

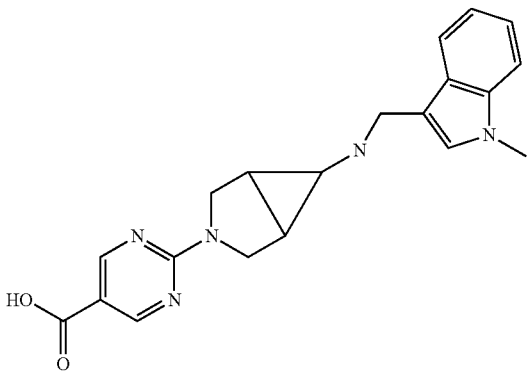 [SMILES: Cn1cc(CNC2C3CN(c4ncc(C(=O)O)cn4)CC32)c2ccccc21]

A mixture of intermediate 5 (1.6 g, 0.00424 mol) and sodium hydroxide 1 M (33.9 mL, 0.034 mol) in MeOH (1.9 mL) and THF (9.8 mL) was stirred at room temperature for 24 hours. The solvents were removed in vacuo and the resultant aqueous solution was acidified to pH: 3-4. The precipitate was filtered and dried, yielding 1.47 g (93%) of intermediate 6.

¹H NMR (400 MHz, d₆-DMSO): 1.8 (br s, 2H); 2 (br s, 1H); 3.5-3.6 (m, 2H); 3.7-3.8 (m, 5H); 4 (br s, 2H); 7 (t, J=7.6 Hz, 1H); 7.15 (t, J=7.6 Hz, 1H); 7.3 (s, 1H); 7.4 (d, J=7.6 Hz, 1H); 7.65 (d, J=7.6 Hz, 1H); 8.7 (s, 2H).

d) Preparation of Intermediate 7

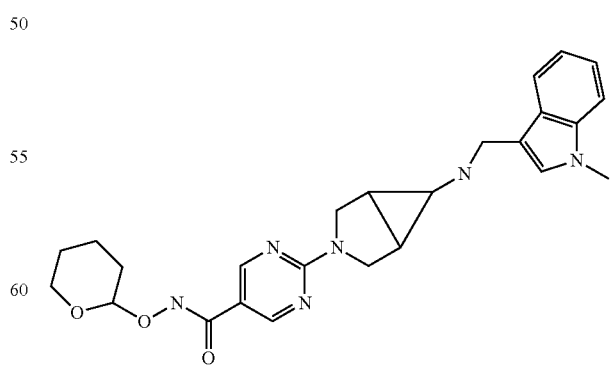

EDC (1.2 g, 0.0077 mol), HOBt (1.044 g, 0.0077 mol) then triethylamine (1.36 mL, 0.0097 mol) and O-(tetrahydro-2H-pyran-2-yl)-hydroxylamine (0.042 g, 0.0097 mol) were added at room temperature to a mixture of intermediate 6 (1.17 g, 0.00322 mol) in DCM (6 mL) and THF (30 mL) under N₂ flow. After stirring at room temperature for 6 days, the solution was poured out into ice water and extracted with DCM. The organic layer was separated, dried (MgSO₄), filtered, and the solvent was evaporated. The residue (0.17 g) was purified by column chromatography over silica gel (15-40 μm) (eluent: DCM/MeOH/NH₄OH 95/5/0.5). The pure fractions were collected and the solvent was evaporated till dryness, yielding 0.7 g (47%) of intermediate 7.

¹H NMR (400 MHz, d₆-DMSO): 1.5-1.73 (m, 8H); 1.8 (s, 1H); 3.5-3.55 (m, 3H); 3.65-3.75 (m, 5H); 3.85 (s, 2H); 3.95-4.05 (m, 1H); 4.9-4.95 (m, 1H); 7.0 (t, J=7.6 Hz, 1H); 7.1 (t, J=7.6 Hz, 1H); 7.2 (s, 1H); 7.35 (d, J=7.6 Hz, 1H); 7.6 (d, J=7.6 Hz, 1H); 8.6 (s, 2H); 11.4 (br s, 1H)

B. Preparation of the Final Compounds

Example B1

Preparation of Compound 1

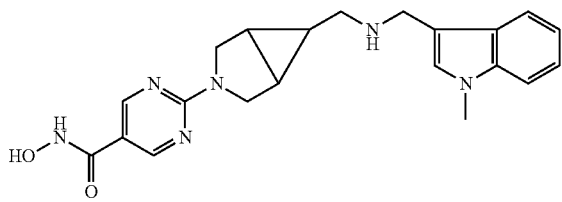 [SMILES: Cn1cc(CNCC2C3CN(c4ncc(C(=O)NO)cn4)CC23)c2ccccc21]

.1.1 C₂HF₃O₂ TFA (78 μL) was added to a mixture of intermediate 3 (16 mg, 0.000034 mol) in MeOH (1.6 mL). The mixture was stirred at room temperature for 24 hours. The solvent was evaporated. The residue was crystallized from diethyl ether. The precipitate was filtered off and dried, yielding 9 mg (52%) of compound 1 as trifluoroacetate salt, melting point: 150° C.

¹H NMR (400 MHz, d₆-DMSO): 0.85-0.95 (m, 1H); 1.8 (s, 2H); 2.95-3.0 (m, 2H); 3.5-3.55 (m, 2H); 3.8 (s, 3H); 3.85 (d, J=11.6 Hz, 2H); 4.3 (s, 2H); 7.1 (t, J=7.6 Hz, 1H); 7.2 (t, J=7.6 Hz, 1H); 7.45-7.5 (m, 2H); 7.75 (d, J=7.6 Hz, 1H); 8.55-8.7 (m, 3H); 9.0 (s, 1H); 11.1 (s, 1H).

Example B2

Preparation of Compound 2

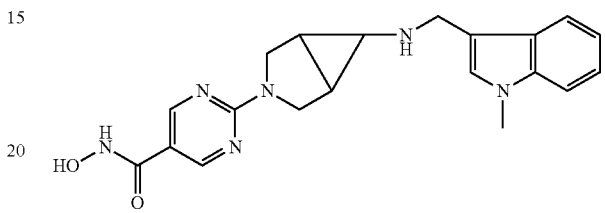

.0.87 C₂HF₃O₂ TFA (0.5 mL) was added at room temperature to a mixture of intermediate 7 (0.1 g, 0.00022 mol) in MeOH (10 mL). The mixture was stirred at room temperature for 24 hours. The solvent was evaporated till dryness. The residue was crystallized from CH₃CN/diethyl ether. The precipitate was filtered off and dried, yielding 90 mg (87%) of compound 2 as trifluoroacetate salt, melting point 157° C.

¹H NMR (400 MHz, d₆-DMSO): 2.15 (s, 2H); 2.55 (s, 1H); 3.5-3.55 (m, 2H); 33.8-3.85 (m, 5H); 4.45 (s, 2H); 7.1 (t, J=7.6 Hz, 1H); 7.2 (t, J=7.6 Hz, 1H); 7.5-7.55 (m, 2H); 7.75 (d, J=7.6 Hz, 1H); 8.65 (s, 2H); 9.1-9.2 (m, 3H); 11.1 (s, 1H).

Table F-1 lists the compounds that were prepared according to one of the above Examples. The following abbreviations were used in the tables: .C₂HF₃O₂ stands for the trifluoroacetate salt.

TABLE F-1

(final compounds)

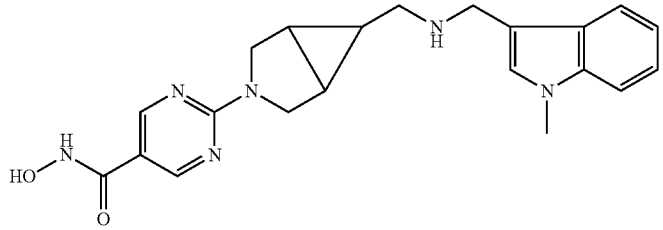

•1.1 C₂HF₃O₂; Co. No. 1; Ex. [B1]; mp: 150° C.

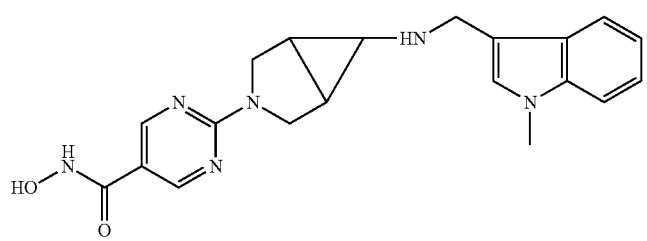

0.87 C₂HF₃O₂; Co. No. 2; Ex. [B2]; mp: 157° C.

TABLE F-1-continued
(final compounds)
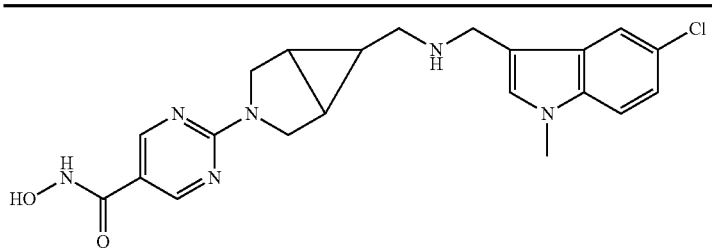
•1.2 C₂HF₃O₂; Co. No. 3; Ex. [B1]; mp: 154° C.
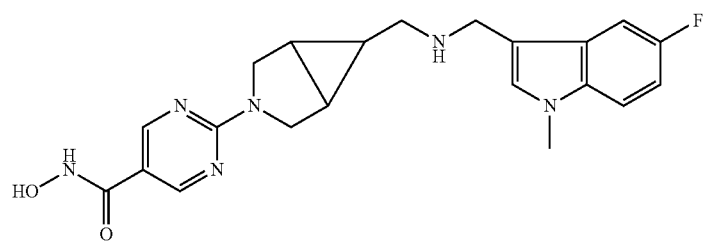
•1.1 C₂HF₃O₂; Co. No. 4; Ex. [B1]; mp: 165° C.
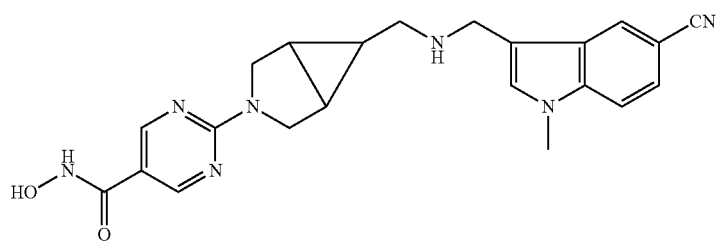
1.3 C₂HF₃O₂; Co. No. 5; Ex. [B1]; mp: 170° C.
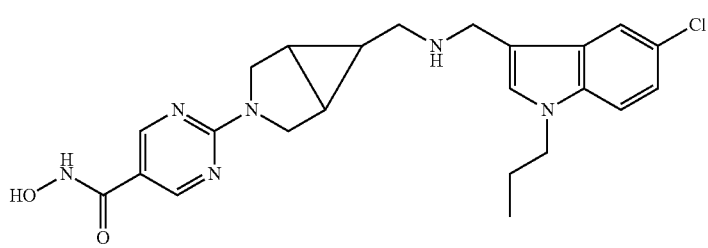
•1.7 C₂HF₃O₂; Co. No. 6; Ex. [B1]; mp: 153° C.
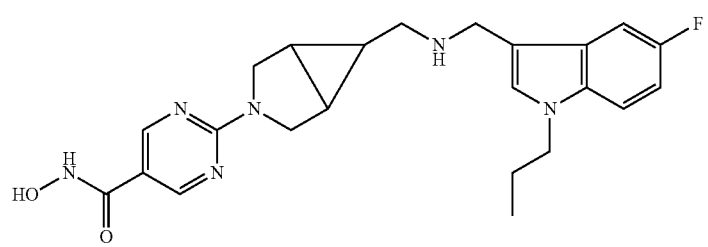
•1.0 C₂HF₃O₂; Co. No. 7; Ex. [B1]; mp: 184° C.

C. Pharmacological Example

The in vitro assay for inhibition of histone deacetylase (see example C.1) measures the inhibition of HDAC enzymatic activity obtained with the compounds of formula (I).

Cellular activity of the compounds of formula (I) was determined on HCT116 tumour cells using a colorimetric assay for cell toxicity or survival (Mosmann Tim, Journal of Immunological Methods 65: 55-63, 1983) (see example C.2).

Example C.1

In Vitro Assay for Inhibition of Histone Deacetylase

Example C.1.a

In Vitro Assay with [$^3$H]-Labelled Substrate

HeLa nuclear extracts (supplier: Biomol) were incubated at 60 μg/ml with 75 μM of substrate. As a substrate for measuring HDAC activity a synthetic peptide, i.e. the amino acids 14-21 of histone H4, was used. The substrate is biotinylated at the $NH_2$-terminal part with a 6-aminohexanoic acid spacer, and is protected at the COOH-terminal part by an amide group and specifically [$^3$H]acetylated at lysine 16. The substrate, biotin-(6-aminohexanoic)Gly-Ala-([$^3$]-acetyl-Lys-Arg-His-Arg-Lys-Val-$NH_2$), was added in a buffer containing 25 mM Hepes, 1 M sucrose, 0.1 mg/ml BSA and 0.01% Triton X-100 at pH 7.4. After 30 min the deacetylation reaction was terminated by the addition of HCl and acetic acid. (final concentration 0.035 mM and 3.8 mM respectively). After stopping the reaction, the free $^3$H-acetate was extracted with ethylacetate. After mixing and centrifugation, the radioactivity in an aliquot of the upper (organic) phase was counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-12}$M. In each test the blank value was subtracted from both the control and the sample values. The control sample represented 100% of substrate deactylation. For each sample the radioactivity was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value) (see Table F-3).

Example C.1.b

In Vitro Assay with Fluorescent-Labelled Substrate

The HDAC Fluorescent Activity Assay/Drug Discovery Kit of Biomol (cat. No: AK-500-0001) was used. The HDAC Fluorescent Activity Assay is based on the Fluor de Lys (Fluorogenic Histone deAcetylase Lysyl) substrate and developer combination. The Fluor de Lys substrate, comprises an acetylated lysine side chain. Deacetylation of the substrate sensitizes the substrate so that, in the second step, treatment with the Fluor de Lys developer produces a fluorophore.

HeLa nuclear extracts (supplier: Biomol) were incubated at 60 μg/ml with 75 μM of substrate. The Fluor de Lys substrate was added in a buffer containing 25 mM Tris, 137 mM NaCl, 2.7 mM KCl and 1 mM $MgCl_2.6H_2O$ at pH 7.4. After 30 min, 1 volume of the developer was added. The fluorophore was excited with 355 nm light and the emitted light (450 nm) was be detected on a fluorometric plate reader.

For each experiment, controls (containing HeLa nuclear extract and buffer), a blank incubation (containing buffer but no HeLa nuclear extract) and samples (containing compound dissolved in DMSO and further diluted in buffer and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-9}$M. All sample were tested 4 times. In each test the blank value was subtracted from both the control and the sample values. The control sample represented 100% of substrate deactylation. For each sample the fluorescence was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value) (see Table F-2).

Example C.1.c

In Vitro Assay for Inhibition of Histone Deacetylase

HeLa nuclear extracts (prepared by high salt extraction of HeLa nuclei, J. D. Dignam et al., S. M. Abmayr et al) were incubated with 9 mg/ml in 0.1M KCl, 20 mM HEPES/NaOH, pH 7.9, 20% (v/v) glycerol, 0.2 mM EDTA, 0.5 mM DTT, 0.5 mM PMSF of enzyme. After 45 min, at 37° C. the deacetylation reaction was terminated. The developer reaction (also at 37° C.) was read in a time dependent manner for an hour. For each experiment, controls (containing HeLa nuclear extract and DMSO without compound) and samples (containing compound dissolved in DMSO and HeLa nuclear extract) were run in parallel. The compounds were tested at concentrations between $10^{-5}$M and $10^{-12}$M. The control sample represented 100% of substrate deactylation. For each sample the activity was expressed as a percentage of the mean value of the controls. Appropriate $IC_{50}$-values (concentration of the drug, needed to reduce the amount of metabolites to 50% of the control) were computed using the Prism program. Herein the effects of test compounds are expressed as $pIC_{50}$ (the negative log value of the $IC_{50}$-value) (see Table F-2). Work was performed by Reaction Biology Corp. (Malvern, Pa., USA).

REFERENCES

1: J. D. Dignam et al. Nucl. Acids Res. 1983, 11, 1475
2: S. M. Abmayr et al. Genes Devel. 1988, 2, 542

Example C.2

Determination of Antiproliferative Activity on HCT116 Cells

Human colon carcinoma HCT116 cells obtained from the ATCC were cultured in McCoy's 5A medium supplemented with 2 mM L-Glutamine, 50 μg/ml gentamicin and 10% heat inactivated fetal calf serum.

Reagents Used in the Alamar Blue Assay

Resazurin was purchased from Aldrich (Prod. No. 199303). Potassium ferrocyanide, potassium ferricyanide, $KH_2PO_4$ and $K_2HPO_4$ were purchased from Sigma (Prod. Nos. P9387, P8131, P5655 and P8281, respectively).

Potassium Phosphate Buffer 0.1 M (PPB) was made as follows: 2.72 gram $KH_2PO_4$ and 13.86 gram $K_2HPO_4$ were dissolved in 500 ml milli-Q $H_2O$, the pH was adjusted to pH 7.4 and the volume was brought to 1 liter with milli-Q $H_2O$; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20× (vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of $4.5 \times 10^3$ cells/ml in Falcon 384-well culture plates (Life Technologies, Merelbeke, Belgium), black with clear bottom, in 45 µl culture medium. Cells were allowed to adhere to plastic for 24 hr. The tested compound was pre-diluted (1/50 in culture medium) and 5 µl pre-diluted compound was added to the wells. Following 4-day incubation, 10 µl of the Alamar Blue solution was added to each well and the cells were further incubated for 4 hrs (HCT116) or 24 hrs (PC-3) at 37° C. The fluorescence intensity was measured for each well on a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, IC50-values (concentration of the drug, needed to reduce cell growth to 50% of the control) were computed using probit analysis for graded data (Finney, D. J., Probit Analyses, 2nd Ed. Chapter 10, Graded Responses, Cambridge University Press, Cambridge 1962). Herein the effects of test compounds are expressed as pIC50 (the negative log value of the IC50-value) (see Table F-2).

TABLE F-2 lists the results of the compounds that were tested according to example C.1. and, C.2.

| Compound number | Enzymatic activity pIC50 C.1.c. | Cellular activity pIC50 C.2 |
| --- | --- | --- |
| 1 | 8.39 | 7.05 |
| 2 | 8.62 | 6.18 |
| 3 |  | 7.12 |
| 4 |  | 7.09 |
| 5 |  | 6.40 |
| 6 |  | 7.45 |
| 7 |  | 7.59 |

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:
1. A compound of formula (I),

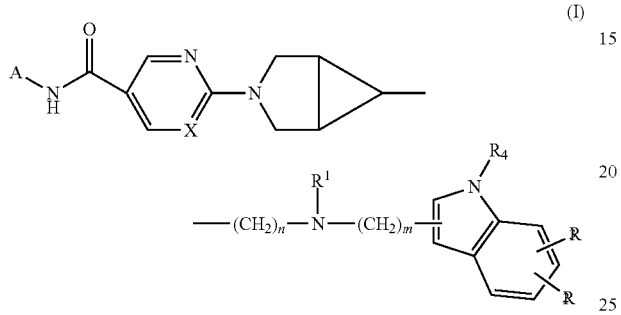

the N-oxide forms, the pharmaceutically acceptable addition salts and the stereo-chemically isomeric forms thereof, wherein
each n is an integer with value 0, 1 or 2 and when n is 0 then a direct bond is intended;
each m is an integer with value 1 or 2;
X is independently N or CH;
A is hydroxy or a radical of formula:

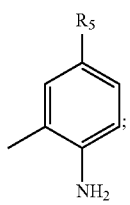

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;
$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;
$R^3$ is hydrogen, halo, $C_{1-6}$alkyl, or $C_{1-6}$alkyloxy; or
when $R^2$ and $R^3$ are on adjacent carbon atoms, they can form the bivalent radical:

—O—CH$_2$—O—    (a-2);

$R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl; or
when $R^2$ is on the 7-position of the indolyl then $R^2$ and $R^4$ together can form the bivalent radical;

—(CH$_2$)$_2$—    (a-3), or

—(CH$_2$)$_3$—    (a-4);

$R^5$ is hydrogen or thiophenyl.

2. A compound as claimed in claim 1 wherein
each n is an integer with value 0 or 1; each m is an integer with value 1; X is independently N; A is hydroxy; $R^1$ is hydrogen; $R^2$ is hydrogen, halo or cyano; $R^3$ is hydrogen; and $R^4$ is $C_{1-6}$alkyl.

3. A compound as claimed in claim 1 wherein
each n is an integer with value 1; each m is an integer with value 1; X is independently N; A is hydroxy; $R^1$ is hydrogen; $R^2$ is hydrogen; $R^3$ is hydrogen; and $R^4$ is $C_{1-6}$alkyl.

4. A compound as claimed in claim 1 having the following structure:

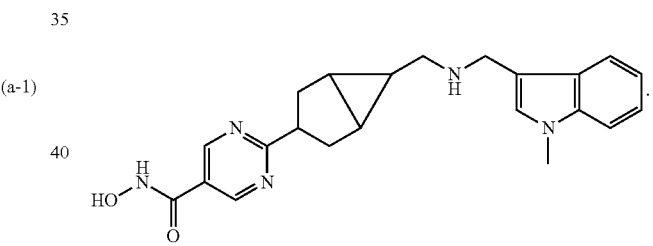

5. A pharmaceutical composition comprising a compound as claimed in claim 1 in a pharmaceutically acceptable carrier.

6. The method of treating colorectal carcinoma, lung adenocarcinoma, breast carcinoma, ovarian carcinoma, prostate cancer, glioma, and fibrosarcoma in a mammal comprising administering an effective amount of a compound of claim 1 to a mammal in need of such treatment.

7. A process for preparing a compound as claimed in claim 1, characterized by
a) reacting an intermediate of formula (II-a), with acid, yielding a hydroxamic acid of formula (I-a)

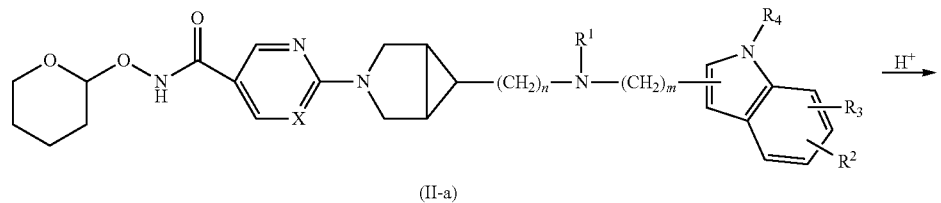

-continued

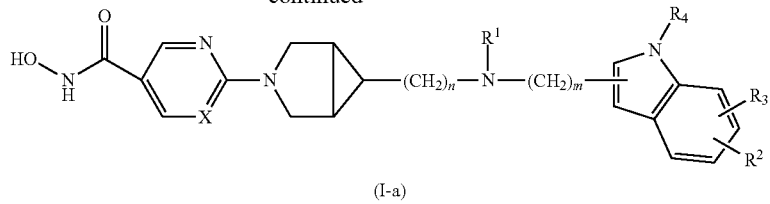
(I-a)

or
b) reacting an intermediate of formula (IV) wherein M represents hydrogen or an alkali metal, with an aniline of formula (III), in the presence of a base and benzotriazol-1-yloxy-tripyrrolidino-phosphonium hexafluorophosphate (PyBOP) in an appropriate solvent $R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;

$R^3$ is hydrogen, halo, $C_{1-6}$alkyl, or $C_{1-6}$alkyloxy; and

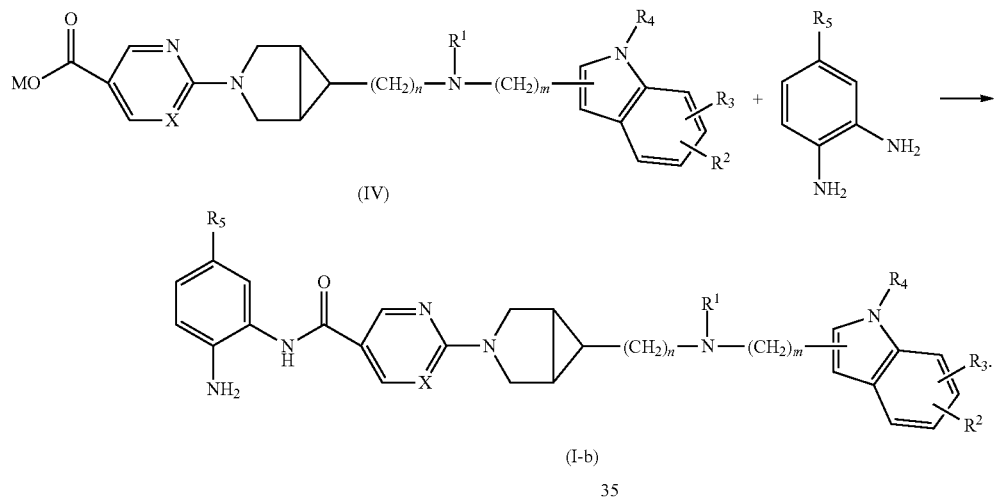

(IV)

(I-b)

8. A compound of formula (II),

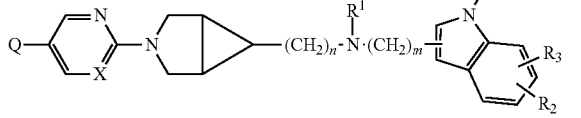

(II)

the N-oxide forms, the pharmaceutically acceptable addition salts and the stereo-chemically isomeric forms thereof, wherein each n is an integer with value 0, 1 or 2 and when n is 0 then a direct bond is intended;

each m is an integer with value 1 or 2;

each X is independently N or CH;

Q is $C_{1-2}$alkyloxycarbonyl, hydroxycarbonyl or tetrahydropyranyloxyaminocarbonyl;

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;

when $R^2$ and $R^3$ are on adjacent carbon atoms, they can form the bivalent radical:

—O—CH$_2$—O— (a-2);

$R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl; or when $R^2$ is on the 7-position of the indolyl then $R^2$ and $R^4$ together can form the bivalent radical;

—(CH$_2$)$_2$— (a-3), or

—(CH$_2$)$_3$— (a-4).

9. A process for preparing a compound as claimed in claim 8, characterized by reacting a compound of formula (II-b) with an intermediate of formula (III) in the presence of N'-(ethylcarbonimidoyl)-N,N-dimethyl-1,3-propanediamine, monohydrochloride (EDC) or 1-hydroxy-1H-benzotriazole (HOBT) with the formation of a compound of formula (II-a), as in the following:

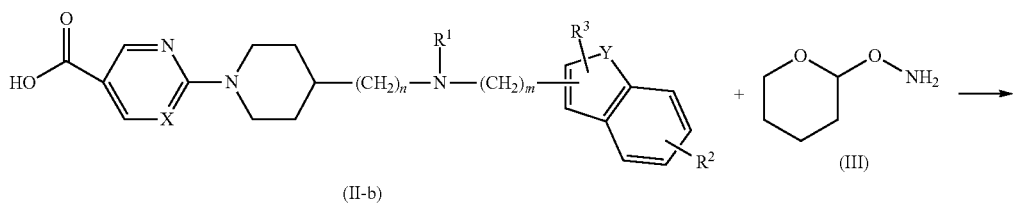

-continued
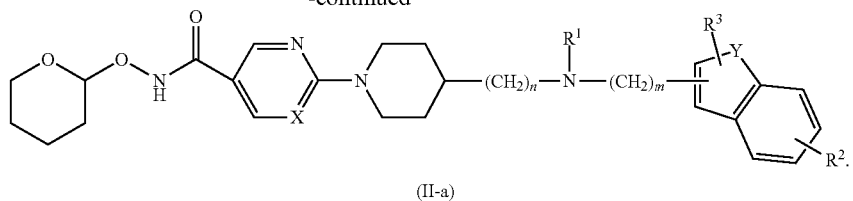
(II-a)
* * * * *